United States Patent [19]
Singh et al.

[11] Patent Number: 5,665,852
[45] Date of Patent: Sep. 9, 1997

[54] SUBSTITUTED UREA AND OXIME MODIFIED AMINO CROSSLINKING AGENTS, CURABLE COMPOSITIONS CONTAINING THE SAME AND PROCESS FOR PREPARING PYRROLIDONE UREA

[75] Inventors: Balwant Singh, Stamford; Laurence W. Chang, Orange; Larry S. Anderson, Bethel, all of Conn.; Stephen F. Donovan, Yardley, Pa.

[73] Assignee: Cytec Technology Corp., Wilmington, Del.

[21] Appl. No.: 480,358

[22] Filed: Jun. 7, 1995

[51] Int. Cl.$^6$ ............ C08L 61/28; C08L 61/32; C08L 61/20
[52] U.S. Cl. ............ 528/254; 528/248; 528/253; 528/256; 528/259
[58] Field of Search ............ 528/254, 248, 528/253, 256, 259

[56] References Cited

U.S. PATENT DOCUMENTS

| | | | |
|---|---|---|---|
| 2,717,908 | 9/1955 | Snyder | 260/534 |
| 3,661,819 | 5/1972 | Koral et al. | 260/21 |
| 4,133,843 | 1/1979 | Isaksen et al. | 260/850 |
| 4,374,771 | 2/1983 | Singh et al. | 260/239.3 R |
| 4,435,559 | 3/1984 | Valko | 528/73 |
| 4,444,954 | 4/1984 | Mels et al. | 525/124 |
| 4,708,984 | 11/1987 | Forgione et al. | 525/127 |
| 4,710,542 | 12/1987 | Forgione et al. | 525/127 |
| 5,084,541 | 1/1992 | Jacobs, III et al. | 528/45 |

FOREIGN PATENT DOCUMENTS

| | | |
|---|---|---|
| 0565925 A1 | 10/1993 | European Pat. Off. . |
| 0604922 A1 | 7/1994 | European Pat. Off. . |
| 2005693 | 8/1971 | Germany . |
| 2010875 | 7/1979 | United Kingdom . |

OTHER PUBLICATIONS

V.E. Marquez, et al., J. Orga. Chem. 45, 5308 (1980).
B. Loev, et al., J. Am. Chem. Soc., 28, 3421-26 (1963).

*Primary Examiner*—W. Robinson H. Clark
*Attorney, Agent, or Firm*—Bart E. Lerman; Claire M. Schultz; Michael J. Kelly

[57] ABSTRACT

Novel substituted urea and oxime carbamate modified amino crosslinking agents, curable compositions containing the same, including curable powder coating compositions, are disclosed. Also disclosed is a novel process for preparing pyrrolidone urea.

7 Claims, No Drawings

SUBSTITUTED UREA AND OXIME MODIFIED AMINO CROSSLINKING AGENTS, CURABLE COMPOSITIONS CONTAINING THE SAME AND PROCESS FOR PREPARING PYRROLIDONE UREA

BACKGROUND OF THE INVENTION

1. Field of the Invention

This invention relates to crosslinking agents and curable compositions containing the same. In particular, the present invention is directed to substituted urea and oxime carbamate modified amino crosslinking agents of triazines or glycolurils. The invention also relates to a novel process for preparing pyrrolidone urea. The invention further relates to curable compositions containing the novel crosslinkers of the invention, including curable powder coating compositions.

2. Related Prior Art

Curable compositions containing amino crosslinking agents have long been known. For example, U.S. Pat. No. 3,661,819 discloses aminotriazine crosslinking agents comprising a triamino compound represented by the formula

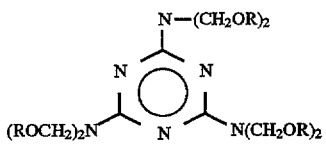

or a benzoquanamine compound represented by the formula

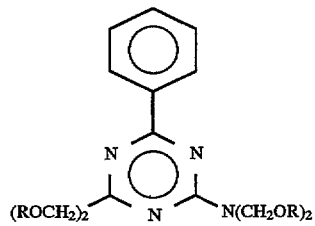

wherein R is hydrogen or alkyl of from 1 to 12 carbon atoms. It is also known to use oligomers of such compounds, which are low molecular weight condensation products containing two, three or four triazine rings, joined, for example, by —$CH_2OCH_2$— and/or —$CH_2$— linkages, as well as mixtures thereof.

These aminotriazine crosslinking agents have been used to self-condense or cure active hydrogen-containing materials, such as polymers containing carboxyl groups, alcoholic hydroxy groups and amide groups. When such curable compositions are applied to substrates as coatings or used as binders for glass fibers or for foundry sand, and then cured, excellent properties in terms of hardness, solvent resistance, tensile strength and so forth are imparted to the article.

Other triazine compounds having excellent properties are also known. For example, U.S. Pat. Nos. 4,708,984 and 4,710,542 disclose amino triazine compounds and oligomers thereof having, respectively, beta-hydroxyalkylcarboxyl methyl and alkylcarbamylmethyl functionality. In addition, aminotriazine crosslinkers having tricarbamoyl functionality are disclosed in U.S. Pat. No. 5,084,541.

U.S. Pat. No. 4,133,843 discloses a process for preparing a curable powder resin which includes the step of condensing a methylol urea or methylolaminotriazine with an aliphatic alcohol having one, two, three or four carbon atoms and a reactive compound containing a hydroxyl or amide. The reactive compounds generally include aliphatic diols and polyols, aliphatic diamides and polyamides, aromatic alcohols, aromatic sulfonamides and phenols. Ureas and carbamates are not disclosed.

A water dispersible coating composition containing an acrylic polymer having active hydrogen functionality and quaternary ammonium salt functionality along with a blocked polyisocyanate is disclosed in U.S. Pat. No. 4,444,954. This patent discloses a multitude of organic polyisocyanate compounds, including triisocyanates, and blocking agents, such as urea and oxime types, which are said to be useful for forming a blocked polyisocyanate. There is no disclosure, or suggestion in this or any of the other patents cited herein of an amino crosslinking agent having substituted urea or oxime blocked carbamate functionality.

SUMMARY OF THE INVENTION

The present invention is directed to an amino crosslinking agent selected from:

(i) a triazine compound represented by the formula (I)

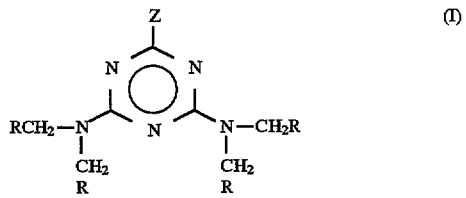

and (ii) a glycoluril compound represented by the formula (II)

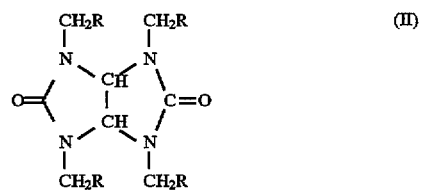

wherein Z is selected from $N(CH_2R)_2$, aryl having 6 to 10 carbon atoms, alkyl having 1 to 20 carbon atoms, cycloalkyl having 6 to 10 carbons and each R is independently selected from the group consisting of (a) a substituted urea represented by the formula $$\underset{B}{\bigcirc}\!\!-\!\!\underset{\|}{\overset{O}{N}}\!\!-\!\!\overset{\|}{C}\!\!-\!\!NH\!\!-$$

wherein B is an unsaturated or saturated aliphatic ring forming group having 3 to 5 carbon atoms optionally substituted by a keto oxygen, or a bridged aromatic ring, (b) an oxime blocked carbamate represented by the formula

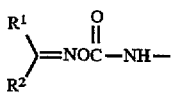

wherein $R^1$ and $R^2$ are independently selected from an alkyl group having 1 to 8 carbon atoms and can form together a cyclic ring having a total of up to 16 carbon atoms including substitution, (c) —$OR^3$, wherein $R^3$ is hydrogen or an alkyl group having 1 to 12 carbon atoms, (d)

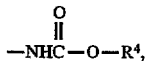

wherein $R^4$ is an alkyl group having 1 to 18 carbon atoms, cycloalkyl group having 6 to 10 carbons or an aryl group having 6 to 20 carbon atoms, and (e)

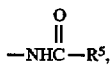

wherein $R^5$ is hydrogen, an alkyl group having 1 to 18 carbon atoms, cycloalkyl group having 6 to 10 carbons or an aryl group having 6 to 20 carbon atoms, provided that at least one R group is selected from (a) or (b). Preferably at least two R groups are selected from (a) and/or (b).

The amino crosslinking agents of this invention can also be an oligomer of (i) or (ii) or a mixture of at least two of (i), (ii) and any oligomers thereof. The degree of substitution of (i) or (ii) by the substituted urea and/or oxime blocked carbamate can vary from about 1 mole of substituent per molecule to full substitution. Preferably, an average of at least about 2 moles of substituted urea and/or oxime blocked carbamate per molecule of crosslinking agent is desired for crosslinking functionality.

The invention is also directed to a curable composition comprising (A) the substituted urea or oxime carbamate modified crosslinking agents of this invention, including oligomers thereof and mixtures of the monomeric crosslinking agents and the oligomers, (B) an active hydrogen-containing material and (C) optionally a cure catalyst. In preferred features of this embodiment of the invention, the, active hydrogen-containing material (B) is a polymeric material containing at least two reactive carboxyl, alcoholic hydroxy, amide or amine groups, or a mixture of such groups, or a group convertible to such groups, preferably a hydroxy-functional acrylic resin, a low molecular weight polyester polyol, or an alkylene polyamine.

Certain crosslinking agents (A) of the present invention which are solids may be advantageously employed in the above-described curable compositions to provide powder curable coating compositions. The pyrrolidone urea modified aminotriazine crosslinking agents of this invention are a particularly preferred example for use in powder coating compositions.

Cure catalysts, when employed, include those well known to one of ordinary skill in the art, such as methyl toluene sulfonimide (MTSI), para-toluene sulfonic acid (P-TSA), metal salts or complexes of metal. Another advantageous aspect of the present invention is the surprising discovery that certain of the crosslinking agents of this invention can cure without cure catalysts even at relatively low cure temperatures, e.g. 190° C.

The amino crosslinking agents of this invention may also be used as self-crosslinkable materials to provide, for example, protective and/or decorative coatings. They also find use in rubber applications, particularly for the maleimido urea modified crosslinking agents which provide improved adhesion of rubber to brass coated steel tire cord. Such crosslinking agents can also be used as toughening agents for rubber, as well as to improve reversion resistance during high temperature cure and/or service.

Yet another embodiment of this invention is directed to articles of manufacture comprising substrates coated with cured compositions obtained from the above-described curable compositions. Also contemplated are articles of manufacture comprising cured compositions of the above-described curable compositions and a filler, such as for example, glass, glass powder, glass beads, glass fiber or foundry sand.

Another aspect of this invention is directed to a novel process for preparing pyrrolidone urea in high yield by reacting 2-pyrrolidone with methyl carbamate or optionally with urea and alcohols.

DETAILED DESCRIPTION OF THE INVENTION

The novel substituted urea and oxime modified amino crosslinking agents of triazines and glycolurils are represented by Formula I and Formula II, respectively. Preferably, the substituted urea group (a) of the crosslinking agents of this invention is selected from the group represented by the formulae

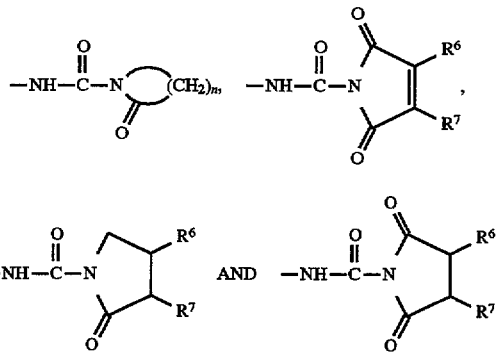

wherein n is 3 to 5, and $R^6$ and $R^7$ are independently hydrogen or alkyl having one to six carbon atoms. More preferably n is 3 or 5, $R^6$ is hydrogen or methyl and $R^7$ is hydrogen. Exemplary substituted urea groups of the crosslinking agents of this invention include those derived from pyrrolidone urea, caprolactam urea, maleimido urea and succinimido urea.

The oxime blocked carbamate group (b) of the crosslinking agents of this invention preferably has $R^1$ and $R^2$ selected from an alkyl group having one to six carbon atoms. More preferably $R^1$ and $R^2$ are independently methyl or ethyl. Exemplary, preferred oxime blocked carbamate groups of the crosslinking agents of this invention include those derived from acetone oxime carbamate, methyl ethyl ketone oxime carbamate and cyclohexanone oxime carbamate.

The novel crosslinking agents of this invention can be prepared by reacting triazine and glycoluril amino resins with substituted ureas or oxime blocked carbamates. While methylolated triazine and glycoluril amino resins are suitable, the alkylated derivatives of those resins are preferred. Generally, the reactants are heated together in the presence of suitable acidic catalysts with the removal of volatile alcohols coproduced in the reaction. The preparation of the novel crosslinking agents of the present invention can be readily accomplished by one of ordinary skill in the art employing well known techniques.

The preferred amino resin starting materials employed to produce the novel crosslinking agents of this invention include alkoxymethyl melamines, alkoxymethyl guanamines, such as aceto-, benzo- and cycloalkyl guanamine, and oligomers thereof. However, hydroxymethyl melamines, hydroxymethyl guanamines such as aceto-, benzo- and cycloalkyl guanamines, and oligomers thereof may also be used if desired. Many of the starting materials are commercially available and can be made by well known procedures.

Particularly suitable amino resin starting materials include, for example, highly methylated melamine-formaldehyde resins available as CYMEL® 300 AND CYMEL® 303, mixed ether and butylated melamine resins available as CYMEL® 1133, and glycoluril resins such as CYMEL® 1172, 1173 and 1174 available from CYTEC Industries Inc., West Paterson, N.J. As noted above, the amino resin starting materials are reacted with substituted ureas or oxime blocked carbamates to obtain the novel crosslinkers of this invention.

Substituted ureas may be obtained by procedures well known to those of ordinary skill in the art. For example, caprolactam urea can be prepared by reacting caprolactam with isocyanic acid as described in Singh, et al., U.S. Pat. No. 4,374,771, the disclosure of which is incorporated by reference herein. As illustrated below, it is also known that pyrrolidone urea may be prepared by reacting 4-aminobutyric acid with potassium cyanate in the presence of hydrogen chloride or alternatively by reacting 4-ureidobutyric acid with POCl₃ [V. E. Marquez, et al., J. Orga. Chem 45, 5308 (1980)].

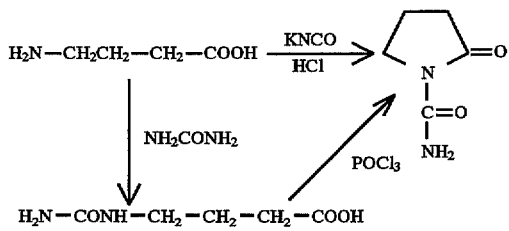

Alternatively, it has been unexpectedly discovered that pyrrolidone urea may also be advantageously prepared in high yield by reacting 2-pyrrolidone with methyl carbamate or optionally with urea and an alcohol (e.g., methanol) as illustrated below:

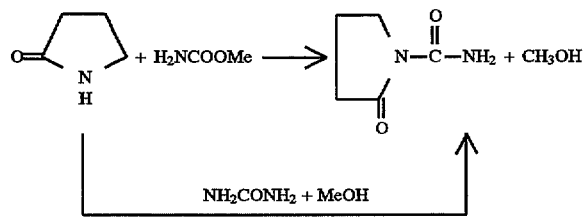

This novel process for preparing pyrrolidone urea is a further embodiment of this invention.

The novel process requires the presence of a catalyst system comprising a tin catalyst and an amine catalyst. Preferably, the amine catalyst is, for example, didecylmethylamine (DAMA-10) available from Ethyl Corporation, Richmond, Va. Exemplary tin catalysts include 1,3-diacetoxy-1,1,3,3-tetrabutyldistannoxane (TK-1 Catalyst) and di-butyltin dilaurate (T-12), both available from Aldrich Chemical Company, Milwauke, Wis. Most preferably, the catalyst system is a mixture of 1,3-diacetoxy-1,1,3,3-tetrabutyldistannoxane and didecylmethylamine. Generally, the amount of tin catalyst and amine catalyst is each in a range from about 0.5 to about 15 percent by weight of the methyl carbamate. Preferably, the range of each is from 0.5 to 5 percent by weight of the methyl carbamate.

The reaction is conducted at a temperature and pressure and for a time sufficient to give the pyrrolidone urea (N-carbamylpyrrolidone). Typically, the reaction mixture employing methyl carbamate is heated to a temperature in a range from about 110° to about 160° C. The reaction can be conducted at ambient pressure or preferably under reduced pressure, e.g., 40–50 mm Hg, to drive the methanol by-product from the reaction mixture without distilling off the methyl carbamate.

If urea and an alcohol, such as methanol, butanol or the like, are employed, then generally the temperature is held in a range from about 80° to about 110° C. and the ammonia produced during the reaction is continually removed. The process, however, may be conducted at any temperature and pressure and for any length of time that results in the production of pyrrolidone urea.

Maleimido urea may be prepared from maleic anhydride and urea as disclosed in U.S. Pat. No. 2,717,908, the disclosure of which is incorporated by reference herein. The oxime carbamate starting materials may also be prepared by methods well known to one of ordinary skill in the art [B. Loev et al., J. Am. Chem. Soc., 28, 3421–26 (1963)].

The degree of substitution of the novel crosslinking agents of this invention is controlled by selecting the mole ratio of the substituted urea or oxime blocked carbamate to the amino resin. Generally, at least one mole of substituted urea or oxime blocked carbamate to one mole of amino resin is used and preferably at least two moles of substituted urea or oxime blocked carbamate per mole of resin is employed to provide crosslinking functionality.

The curable compositions of this invention comprise (A) the substituted urea or oxime carbamate modified crosslinking agents and/or oligomers thereof, (B) an active hydrogen-containing material and (C) optionally a cure catalyst. The active hydrogen-containing materials employed in this process include those known to one skilled in the art which have at least one active-hydrogen moiety selected from the group consisting of carboxyl, hydroxy, thiol, sulfonamide, amido, primary amine, secondary amine (including imine), salts thereof and mixtures thereof. The active hydrogen-containing materials useful herein are typically film-forming compositions, which form polymeric back-bones in the resultant cured compositions. Illustrative examples of active hydrogen-containing materials are shown in U.S. Pat. No. 4,435,559, the disclosure of which is incorporated by reference herein. Typical of such materials are acrylic polymers, polyesters, epoxy resins, alkylene polyamines, such as hexamethylene diamine, and the like.

Especially suitable active hydrogen containing materials include polyesters and polyacrylates containing pendant hydroxyl groups as reaction sites. The former are obtained in a known manner by, for example, the reaction of polycarboxylic acids with excess quantities of polyhydric alcohols; the latter are obtained by the copolymerization of acrylic or methacrylic acid derivatives with hydroxyl-group-containing derivatives of these acids, such as, for example, the hydroxyalkyl esters, optionally with the simultaneous use of additional vinyl compounds, such as, for example, styrene. Hydroxyl-group-containing polyurethanes can be obtained in a known manner by the reaction of polyisocyanates with excess quantities of compounds containing at least two hydroxy groups. Suitable commercially available hydroxy-group-containing polyesters are CYPLEX® 1531 a polyester of phthalic acid, adipic acid, ethanediol, and trimethylolpropane available from CYTEC Industries, Cargil Polyester 3000, 3016, 3018, 3020 and 5776, available from Cargil and TONE 0200 available from Union Carbide Corp. Suitable hydroxy functional acrylic resins are available commercially from S. C. Johnson & Son, Inc. under the trademark JONCRYL®-500, a copolymer of 50% styrene, 20% hydroxypropyl methacrylate and 30% butyl acrylate, and from Rohm & Haas. Co. under the trademark AT-500. Also suitable for use are hydroxy-terminated polycaprolactones.

The curable composition optionally also includes a cure catalyst. Such cure catalysts are well known to those skilled in the art and include, for example, methyl toluene sulfonimide (MTSI) and para-toluene sulfonic acid (P-TSA). Other typical cure catalysts include a metal salt and/or complex of a metal such as lead, zinc, iron, tin, titanium and manganese, preferably tin. Suitable salts of these metals are, for example acetates, octoates, laurates and naphthanates. Preferred tin catalysts are tetrabutyldiacetoxy stannoxane (1,3-diacetoxy-1,1,3,3-tetrabutyldistannoxane), dibutyltin dilaurate, dimethyltin dilaurate. Suitable complexes are the acetyl acetonates of iron, cobalt and the like.

Quaternary and ternary compounds may also be utilized as catalysts. Generally, the ternary or quaternary catalysts are known compounds of the formulas:

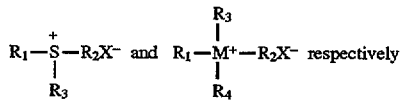

wherein $R_1$, $R_2$, $R_3$ and $R_4$ may be equivalent or different and may be $C_1$ to $C_{20}$ aliphatic, aromatic, benzylic, cyclic aliphatic and the like, where M may be nitrogen, phosphorous or arsenic (to provide, respectively, quaternary ammonium, phosphonium or arsonium compounds), where S is sulfur (to provide a ternary sulfonium compound), and where $X^-$ may be hydroxide, alkoxide, bicarbonate, carbonate, formate, acetate lactate, and other carboxylates derived from volatile organic carboxylic acids or the like.

When employed, the cure catalyst is used in the curable compositions of this invention in amounts effective to accelerate cure at the temperature employed. For example, the catalyst is typically used in amounts of from about 0.01 to about 2.0% by weight based on the weight of the curable compositions.

In the practice of the invention, the curable compositions can be adapted for use in solvent-based, water-based, and powder coating compositions depending on the properties, e.g., liquid or solid, of the particular substituted urea or oxime carbamate modified amino crosslinking agent. Coating compositions comprising aqueous dispersions are particularly suited to application by electrodeposition. Typically, the compositions will contain about 1 to 90 percent, by weight, of combined active hydrogen-containing material and crosslinker and the weight ratio crosslinker:active hydrogen-containing material will range from about 5:95 to about 50:50. Preferably, depending on the relative equivalent weights of the crosslinker and active hydrogen-containing material, the weight ratios would be from about 15 to 40 parts crosslinker to about 60 to 85 parts active hydrogen-containing material.

The solid substituted urea and oxime carbamate modified triazines and glycoluril crosslinking agents of this invention can be advantageously employed in curable powder coating compositions. A particularly preferred crosslinking agent for use in powder coatings is a pyrrolidone urea modified alkoxymethyl melamine. Preferably the molar ratio of pyrrolidone urea to the melamine resins is from about 2:1 to about 3:1. Fully substituted melamine resins, i.e., 6 moles of pyrrolidone urea per mole of melamine resin, may require temperatures in excess of 160° C. to achieve practical cure states. The curable powder coating compositions of this invention containing pyrrolidone urea partially substituted alkoxymethyl melamines were found to advantageously cure without the need of a cure catalyst at relatively low cure temperatures, e.g., about 175°–200° C., preferably about 190° C. These cured films have substantially equivalent physical and chemical properties compared to films derived from prior art powder coating compositions without the necessity of expensive cure catalysts.

In many instances, a pigment composition and various other conventional additives such as antioxidants, surface active agents, coupling agents, flow control additives, and the like, can be included in the curable composition of this invention. The pigment composition may be of any conventional type, such as iron oxides, lead oxides, strontium chromate, carbon black, titanium dioxide, talc, barium sulfate, cadmium yellow, cadmium red, chromic yellow, or the like.

For example, a typical curable powder coating composition may contain about 20 weight percent of a pigment such as titanium oxide (e.g., R-960 available from E. I. du Pont de Nemours & Co.) and about 0.5 to about 1.0 weight percent of catalyst, if desired or necessary, based on the combined weight of crosslinker and active hydrogen-containing backbone. In addition, a typical composition may also contain flow control additives, such as RESIFLOW® P 67 (an acrylic polymer absorbed on silica available from Estron Corp.) and benzoin, each in an amount of about 1 weight percent based on the total weight of the crosslinker, backbone, and titanium oxide pigment. The weight ratio of the crosslinking agent and the active hydrogen-containing material in the powder coating composition will depend on the equivalent weights of these two components and can be readily ascertained by one of ordinary skill.

The amount of crosslinking agent employed is typically in the range from about 3 to about 30 weight percent, and preferably in the range of from about 6 to about 15 weight percent based on the combined weight of the crosslinking agent and active hydrogen-containing material. Conversely, the amount of active hydrogen-containing material is typically in the range of from about 70 to about 97 weight percent, and preferably in the range of about 85 to about 95 weight percent of their combined weight.

The powder coating composition of the present invention can be used by depositing the powder coating composition on a substrate by any well-known means such as a powder gun, electrostatic depositions or deposition from a fluidized bed. After application to a substrate, such as a steel panel, the powder coating composition is heated to a temperature sufficient to cause the particles to flow and cure by any conventional method, such as in baking ovens or with banks of infrared heat lamps or any other means available to those skilled in the art. Depending on the particular selection of components, the powder is heated to temperatures between about 110° C. and about 230° C., preferably between about 150° C. and about 230° C., and more preferably about 170° C. to about 200° C.

Conventional methods may also be used to combine the novel crosslinking agents herein with fillers and/or reinforcements and to shape them into useful articles by means well known to those of ordinary skill in the art.

The examples which follow are intended as an illustration of certain preferred embodiments of the invention, and no limitation of the invention is implied.

EXAMPLE 1

Reaction Product of 6 Moles of Caprolactam Urea With 1 Mole of Hexamethoxymethylmelamine (6-CLU)

Hexamethoxymethylmelamine (10.80 g, 0.028 mole, CYTEC Industries, CYMEL® 300), caprolactam urea (25.83 g, 0.166 mole), and para-toluenesulfonic acid (0.28 g) were stirred at 95° C. in a flask equipped with a vacuum distillation head. During a 60 minute period, the pressure was lowered in stages to 50 mm Hg and 4.71 g of methanol (0.147 mole, 89% of theoretical) was collected in the distillate receiver. The product in the reaction flask was cooled to near room temperature to obtain a clear colorless solid. Methylene chloride (175 ml) was added and the product dissolved after one-half hour of stirring. The acid catalyst was removed by washing with sodium carbonate solution, followed by drying over potassium carbonate. Rotary vacuum evaporation gave 31.75 g, 99% yield, of a clear colorless solid having a melting point of 88°–90° C. Nuclear magnetic resonance (NMR) analysis showed that the product had at least five (on average) of the methoxy groups replaced by caprolactam urea groups.

EXAMPLE 2

Reaction Product of 2 Moles of Caprolactam Urea With 1 Mole of Hexamethoxymethylmelamine (2-CLU)

Hexamethoxymethylmelamine (22.97 g, 0.0589 mole, CYTEC Industries, CYMEL ® 300), caprolactam urea (18.38 g, 0.118 mole), and para-toluenesulfonic acid (0.31 g) were stirred at 95° C. in a flask equipped with a vacuum distillation head. During a 120 minute period, the pressure was lowered in stages to 50 mm Hg and 3.70 g of methanol (0.116 mole, 98% of theoretical) was collected in the distillate receiver. The product in the reaction flask was cooled to near room temperature to obtain a clear colorless viscous liquid. Methylene chloride (200 ml) was added and the product dissolved after one-half hour of stirring. The acid catalyst was removed by washing with sodium carbonate solution, followed by drying over 3 Angstrom molecular sieves. Rotary vacuum evaporation gave 36.80 g, 98% yield, of a clear colorless viscous liquid. Infrared spectroscopy showed the replacement of methoxy groups by the urea $NH_2$ groups.

EXAMPLE 3

Reaction Product of 1 Mole of Caproluctum Urea With 1 Mole of Hexamethoxymethylmelamine (1-CLU)

A caprolactam urea modified hexamethoxymethylmelamine crosslinking agent (1-CLU) was prepared with a ratio of 1 mole of caprolactam urea to one mole of hexamethoxymethylmelamine, CYTEC Industries, CYMEL®300, in a manner similar to Example 1 by adjusting the molar ratio of caprolactam urea and hexamethoxymethylmelamine.

The crosslinking agents prepared in Examples 1–3 were formulated into curable compositions with a polyacrylate resin, applied to iron phosphate treated steel panels (B-1000) and cured in a high temperature oven. The resulting films were subjected to an MEK (methyl ethyl ketone) double-wipe test. The components of each composition, the cure parameters and the results of the MEK double-wipe test (MEK WIPES) are set forth in Table 1 below.

TABLE 1

| | Composition (parts by weight) | | | | | |
|---|---|---|---|---|---|---|
| | 1A | 1B | 1C | 1D | 1E | 1F |
| Polyacrylate | 70 | 70 | 70 | 70 | 70 | 70 |
| Ex. 1 (6-CLU) | 30 | 30 | 30 | — | — | — |
| Ex. 2 (2-CLU) | — | — | — | — | 30 | 30 |
| Ex. 3 (1-CLU) | — | — | — | 30 | — | — |
| TBDAS* | — | 1 | — | — | — | 1 |
| p-TSA** | — | — | 1 | 1 | 1 | — |
| Cure Temp., °C. | 175 | 175 | 175 | 125 | 125 | 150 |
| Cure Time, Min. | 30 | 30 | 30 | 20 | 20 | 20 |
| MEK WIPES | >200 | >200 | >200 | >200 | >200 | fail |

*1,3-Diacetoxy-1,1,3,3-tetrabutyldistannoxane
**para-toluene sulfonic acid
Note:
Composition 1A, 1B and 1C failed the MEK wipe test when the cure temperature was 150° C. for 30 minutes.

The results show that curable compositions containing caprolactum urea modified melamine crosslinking agents and a polyacrylate active hydrogen-containing material provide cured films having good solvent resistance properties with the selection of appropriate cure catalysts, if any, cure temperature and time.

EXAMPLE 4

Reaction Product of 6 Moles of Pyrrolidone Urea With 1 Mole of Hexamethoxymethylmelamine (6-PYU)

Hexamethoxymethylmelamine (1.15 g, 0.0029 mole, CYTEC Industries, CYMEL® 300), pyrrolidone urea (2.20 g, 0.0172 mole), para-toluenesulfonic acid (0.09 g), and 25 ml of toluene were stirred at 90° C. in a flask equipped with a vacuum distillation head. During a 60 minute period, the pressure was lower in stages to 5 mm Hg and the solvent was removed. Methylene chloride (50 ml) was added and the product dissolved after one-half hour of stirring. Filtration followed by rotary vacuum evaporation gave a clear product. Infrared spectroscopy showed the replacement of methoxy groups by the urea $NH_2$ groups.

EXAMPLE 5–6

Reaction Product of 4 Moles and 2 Moles of Pyrrolidone Urea With 1 Mole of Hexamethoxymethylmelamine (4-PYU & 2-PYU)

Pyrrolidone urea modified hexamethoxymethylmelamine crosslinking agents (4-PYU and 2-PYU) were prepared respectively, using a ratio of 4 moles of pyrrolidone urea and 2 moles of pyrrolidone urea to one mole of hexamethoxymethylmelamine, CYTEC Industries, CYMEL® 300, in a manner similar to Example 4 by adjusting the molar ratio of caprolactum urea and hexamethoxymethylmelamine.

The crosslinking agents prepared in Examples 4–6 were formulated into curable compositions with a polyacrylate active hydrogen-containing material, applied to iron phosphate treated steel panels (B-1000) and cured in a high temperature oven. The components of each formulation, the cure parameters and the results of MEK double-wipe tests are set forth in Table 2 below.

TABLE 2

| Composition (parts by weight) | | | |
|---|---|---|---|
| | 2A | 2B | 2C |
| Polyacrylate | 70 | 70 | 70 |
| Ex. 4 (6-PYU) | — | — | 30 |
| Ex. 5 (4-PYU) | — | 30 | — |
| Ex. 6 (2-PYU) | 30 | — | — |
| TBDAS* | 1 | 1 | 1 |
| Cure Temp., °C. | 175 | 175 | 175 |
| Cure Time, Min. | 20 | 20 | 20 |
| MEK WIPES | >200 | >200 | >200 |

*1,3-Diacetoxy-1,1,3,3-tetrabutyldistannoxane
Note:
The compositions failed the MEK wipes test when the cure temperature waas 150° C. for 20 minutes.

The results show that curable compositions containing pyrrolidone urea modified melamine crosslinking agents and a polyacrylate active hydrogen-containing material provide cured films having good solvent resistance.

EXAMPLE 7

Reaction Product of 3 Moles of MEK Oxime Carbamate With 1 Mole of Hexamethoxymethylmelamine (3-MOC)

Hexamethoxymethylmelamine (33.0 g, 0.0846 mole, CYTEC Industries, CYMEL® 300), MEK oxime carbamate (34.6 g, 0.2662 mole), para-toluenesulfonic acid (0.95 g), and 100 ml of methylene chloride were stirred in a flask equipped with a vacuum distillation head in a 75° C. oil bath. During a 6 hour period, the pressure was lowered in stages to 5 mm Hg and the solvent was removed. Methylene chloride was added and the viscous product dissolved after one-half hour of stirring. The acid catalyst was removed by washing with sodium bicarbonate solution. Rotary vacuum evaporation gave a clear product. Infrared spectroscopy shows no starting oxime carbamate $NH_2$ groups, and nuclear magnetic spectroscopy (NMR) analysis showed that the product had 2.8 of the methoxy groups replaced by MEK oxime carbamate.

EXAMPLE 8–9

Reaction Product of 5.5 Moles and 4 Moles of MEK Oxime Carbamate With 1 Mole of Hexamethoxymethylmelamine (5.5-MOC & 4-MOC)

Methyl ethyl ketone (MEK) oxime carbamate modified hexamethoxymethylmelamine crosslinking agents (5.5-MOC and 4 MOC) were prepared, respectively, with a ratio of 5.5 moles of MEK oxime carbamate and 4 moles of MEK oxime carbamate to one mole of hexamethoxymethylmelamine, CYTEC Industries, CYMEL® 300, in a manner similar to Example 7 by adjusting the molar ratio of MEK oxime carbamate and hexamethoxymethylmelamine.

The crosslinking agents prepared in Examples 8–9 were formulated into curable compositions, applied to iron phosphate treated steel panels (B-1000) and cured in a high temperature oven. The components of each formulation, the cure parameters and the results of MEK double-wipe tests are set forth in Table 3 below.

TABLE 3

| Compostion (parts by weight) | | | | | | | |
|---|---|---|---|---|---|---|---|
| | 3A | 3B | 3C | 3D | 3E | 3F | 3G |
| Polyacrylate | 60 | 0 | 60 | — | — | — | — |
| Ex. 8 (5.5-MOC) | 40 | 40 | — | — | — | — | — |
| Ex. 9 (4.0-MOC) | — | — | 40 | 40 | 30 | 40 | 50 |
| CYPLEX® 1473** | — | 60 | — | 60 | 70 | 60 | 50 |
| TBDAS* | 1 | 1 | 1 | 1 | 1 | 1 | 1 |
| Cure Temp., °C. | 135 | 135 | 135 | 135 | 150 | 150 | 150 |
| Cure Time, Min. | 30 | 30 | 30 | 30 | 20 | 20 | 20 |
| MEK WIPES | >200 | >200 | >200 | >200 | >200 | >200 | >200 |

*1,3-Diacetoxy-1,1,3,3-tetrabutyldistannoxane
**CYPLEX® 1473 - hydroxy group-containing polyester available from CYTEC Industries, Inc., West Patterson, New Jersey
Note:
Composition 3A–3D failed the MEK wipes test when the cure temperature was 130° C. for 30 minutes.

The results show that curable compositions containing MEK oxime carbamate modified melamine crosslinking agents and active hydrogen-containing material provide cured films having good solvent resistance.

EXAMPLE 10

Reaction Product of 3 Moles of N-Propyl Carbamate (PC) and 3 Moles of Maleimide Urea (MU) with 1 Mole of Hexamethoxymethylmelamine (3-PC, 3-MU)

Hexamethoxymethylmelamine (2.77 g, 0.0071 mole, CYTEC Industries, CYMEL® 300), n-propyl carbamate (2.20 g, 0.0214 mole), maleimide urea (3.00 g, 0.0214 mole), para-toluenesulfonic acid (0.025 g), and 30 ml acetonitrile were stirred at reflux for 5 hours in a flask equipped with a vacuum distillation head. The solvent was stripped under vacuum to give a white solid. Methylene chloride (50 ml) was added and the product dissolved after one-half hour of stirring. The acid catalyst was removed by washing with sodium carbonate solution, followed by drying over potassium carbonate. Rotary vacuum evaporation gave 6.6 g, 100% yield, of a clear colorless solid that melted at 115°–130° C.

EXAMPLE 11

Reaction Product of 5 Moles of Maleimido Urea With 1 Mole of Hexamethoxymethylmelamine (5-MU)

Hexamethoxymethylmelamine (13.3 g, 0.341 mole, CYTEC Industries, CYMEL® 300), maleimido urea (23.5 g, 0.1679 mole), phosphoric acid (0.5 g), and 100 ml methanol were stirred in a flask. The methanol was removed by rotary evaporation, and the reaction vessel was immersed in a 85° C. oil bath and stirred under a 2 mm Hg vacuum for 17 hours. The solvent was stripped under vacuum to give a white solid. Methylene chloride (300 ml) and 20 g of potassium carbonate were added and stirred. The cloudy solution was filtered through celite and dried over magnesium sulfate (5 g). Filtering and rotary evaporation gave 23.2 g, 75% yield, of a solid. Infrared spectroscopy showed the replacement of methoxy groups by the amide $NH_2$ groups.

EXAMPLE 12–13

Reaction Product of 4 Moles and 2 Moles of Maleimido Urea With 1 Mole of Hexamethoxymethlmelamine (4-MU & 2-MU)

Maleimido urea modified hexamethoxymethylmelamine crosslinking agents (4-MU ad 2-MU) were prepared with, respectively, 4 moles of maleimido urea and 2 moles of maleimido urea to mole of hexamethoxymethylmelamine, CYTEC Industries, CYMEL® 300, in a manner similar to Example 11 by adjusting the molar ratio of maleimido urea and hexamethoxymethylmelamine.

The maleimido urea modified melamine crosslinking agents of Examples 12 and 13 were formulated into curable compositions with a polyacrylate active hydrogen-containing material, applied to iron phosphate treated steel panels (B-1000) and heated in a high temperature oven. The composition of the formulation, the cure parameters and the results of MEK double wipe tests is set forth in Table 4 below.

TABLE 4

| | Composition (parts by weight) | | | | | | | |
|---|---|---|---|---|---|---|---|---|
| | 4A | 4B | 4C | 4D | 4E | 4F | 4G | 4H |
| Polyacrylate | 70 | 70 | 70 | 70 | 70 | 70 | 70 | 70 |
| Ex. 12 (4-MU) | 30 | 30 | 30 | 30 | — | — | — | — |
| Ex. 13 (2-MU) | — | — | — | — | 30 | 30 | 30 | 30 |
| TBDAS* | — | 1 | — | 1 | — | 1 | — | 1 |
| Cure Temp., °C. | 150 | 150 | 160 | 160 | 150 | 150 | 160 | 160 |
| Cure Time, Min. | 20 | 20 | 20 | 20 | 20 | 20 | 20 | 20 |
| MEK WIPES | 0 | 20 | 10 | 100 | 0 | 75 | 10 | 200 |

*1,3-Diacetoxy-1,1,3,3-tetrabutyldistannoxane

The results show that curable compositions containing maleimido urea modified hexamethoxymethylmelamine crosslinking agents having a molar ratio of about 2 maleimido urea groups to 1 mole of melamine provide cured films having good solvent resistance when used with a cure catalyst and cured at about 160° C. The maleimido urea modified melamine crosslinkers did not cure well in the absence of a cure catalyst, even at a cure temperature of 160° C.

EXAMPLE 14

Reaction Product of 4 Moles of Pyrrolidone Urea With 1 Mole of Hexamethoxymethylmelamine (4-PYU)

Pyrrolidone urea (25 g, 0.20 mole) was dissolved in 250 ml of warm (40° C.) methanol. A homogeneous solution was obtained by adding Hexamethoxymethylmelamine, CYTEC Industries, CYMEL® 303 (386 g, 0.76 mole) and para-toluenesulfonic acid (1.1 g). The solution was stripped of methanol under reduced pressure, and the residue was heated to 95° C. in an oil bath under vacuum for 1.5 hours. The reaction mixture was allowed to cool to room temperature, followed by the addition of 300 ml toluene. The toluene solution was washed with two portions of 200 ml 5% aqueous sodium carbonate solution and 250 ml water. The washed toluene solution was dried over magnesium sulfate and the toluene was stripped. The residue, a white solid, weighted 47.2 g (83% yield).

EXAMPLE 15–18

Reaction Product of 3 Moles and 2 Moles of Pyrrolidone Urea With 1 Mole of Hexamethoxymethylmelamine (3-PYU and 2-PYU)

A series of four pyrrolidone urea modified melamine crosslinking agents for powder coatings were prepared by reacting hexamethoxymethylmelamine, CYTEC Industries, CYMEL® 300 and CYMEL® 303 at a melamine to pyrrolidone ratio of 1:2 and 1:3 in a manner similar to Example 14. The properties of the resulting crosslinking agents are set forth in Table 5.

TABLE 5

| | Pyrrolidone Urea Modified Melamine Crosslinking Agents | | | | | | | |
|---|---|---|---|---|---|---|---|---|
| Crosslinker | Hexamethoxymethyl-melamine resin (HMMM) | Ratio of HMMM/PYU* Reacted | mp(°C.) | Ratio of OMe/PYU$^a$ Round | $Mn^b$ | $Mw^b$ | Mw/Mn | Tg(°C.)$^c$ |
| Ex. 15 | CYMEL ® 300 | 1:2 | 46–61 | 1.6 | 700 | 900 | 1.3 | 31 ± 1 |
| Ex. 16 | CYMEL ® 300 | 1:3 | 65–75 | 1.1 | 600 | 1000 | 1.7 | 30 ± 1 |
| Ex. 17 | CYMEL ® 303 | 1:2 | 70–93 | 1.7 | 900 | 1,600 | 1.8 | 35 ± 1 |
| Ex. 18 | CYMEL ® 303 | 1:3 | 75–90 | 1.3 | 700 | 1,100 | 1.6 | 35 ± 1 |

*HMMM/PYU = hexamethoxymethylmelamine/pyrrolidone urea
$^a$determined by nuclear magnetic resonance spectroscopy
$^b$determined by high performance size exclusion chromatography
$^c$determined by differential scanning colorimeter
Note:
CYMEL ® 300 - Mn = 390, Mw = 450, Mw/Mn = 1.2
CYMEL ® 303 - Mn = 500, Mw = 700, Mw/Mn = 1.4

Powder coating compositions were prepared containing the pyrrolidone urea modified melamine crosslinking agents of Examples 15–18 and hydroxyl terminated polyesters.

The components of the compositions were mixed and blended in a high-intensity mixer. The blended mixture was then melt-mixed on a two-roll mill. (The temperature of one roll was kept at 130° C. and the other was kept at 15° C.). The melt-mixed material was allowed to cool to room temperature and hand ground (with pestle and mortar) to fine powder. A thin layer of a curable powder paint composition was then placed on iron phosphate treated steel panels (B-1000), and the panels were heated in a high temperature oven for 20 minutes. The baked compositions were then subjected to MEK double-wipes tests. The compositions showing good MEK solvent resistance (greater than 200 MEK double wipes) in the drawdown method were also prepared in a larger quantity. In these cases, the compositions after having been melt-mixed in a two-roll mill were chopped and crushed in a Waring Blender followed by grinding and classification in a mill-classifier. The ground compositions which had a particle size of approximately 35±10μ were then electrostatically sprayed on B-1000 panels and cured in ovens. The powder coating compositions and MEK Wipes test results for these compositions are illustrated in Table 6.

TABLE 6

| Polyester/X-Linker (Molar Ratio) | Catalyst (%)[a] | Method[b] | Bake T, °C. | MEK Rubs[c] |
|---|---|---|---|---|
| PE-1/Ex. 15 (88/12) | MTSI (0.5) | D | 190 | e |
|  |  | D | 200 | e |
| PE-2/Ex. 15 (92/8) | TK-1 (0.5) | D | 175 | >200 |
|  |  | D | 190 | >200 |
|  |  | D | 200 | >200 |
| PE-2/Ex. 15 (92/8) | — | D | 190 | >200 |
| PE-2/Ex. 15 (92/8) | — | S | 175 | >200 |
|  |  |  | 190 | >200 |
| PE-2/Ex. 15 (92/6) | — | D | 200 | 100 |
| PE-2/Ex. 15 (84/15) | — | S | 175 | >200 |
| PE-1/PE-2/Ex. 15 (46/46/8) | — | S | 175 | 2 |
|  |  |  | 190 | >200 |
|  |  |  | 200 | >200 |
| PE-1/PE-2/Ex. 15 (42.6/43.2/7.4) | — | S | 190 | >200 |
|  |  |  | 200 | >200 |
| PE-4/Ex. 15 (92/8) | — | D | 190 | >200 |
|  |  | D | 200 | >200 |
| PE-4/Ex. 15 (91/9) | — | S | 190 | >200 |
|  |  |  | 200 | >200 |
| PE-5/Ex. 15 (93/7) | — | D | 190 | NC |
|  |  | D | 200 | NC |
| PE-2/PE-5/Ex. 15 (46/46/8) | — | D | 190 | >200 |
|  |  | D | 200 | >200 |
| PE-2/PE-5/Ex. 15 (46/46/8) | — | S | 190 | >200 |
|  |  |  | 200 | >200 |
| PE-5/Ex. 15 (92/8) | — | D | 190 | e |
|  |  |  | 200 | e |
| PE-4/Ex. 18 (92/8) | — | D | 190 | >200 |
| PE-4/Ex. 18 (92/8) | — | S | 190 | 100 |
|  |  |  | 200 | 120 |
| PE-4/Ex. 17 (92/8) | — | D | 190 | >200 |
|  |  |  | 200 | >200 |
| PE-4/Ex. 17 (94/6) | — | D | 190 | >200 |
| PE-4/Ex. 17 (92.5/7.5) | — | S | 200 | >200 |
| PE-3/Ex. 17 (90/10) | — | D | 190 | >200 |
| PE-1/Ex. 17 (91/9) | — | D | 200 | e |
| PE-3/Ex. 17 (90/10) | — | S | 190 | >200 |
|  |  |  | 200 | >200 |
| PE-3/Ex. 17 (90/10) | DABCO (0.5) | D | 190 | >200 |
|  |  |  | 200 | >200 |
| PE-3/Ex. 17 (90/10) | DABCO (0.5) | D | 190 | >200 |
|  |  |  | 200 | >200 |

[a]Based on the combined weight of crosslinker and backbone
[b]D = Drawdown; S = Electrostatic spray
[c]MEK double wipe
[d]Determined by DSC - differential scanning calorimeter
[e]Not cured
Hydroxyl terminated polyesters:
PE-1:Arakote ® 3109 (Ciba-Geigy Corp.)
PE-2:Cargill ® 3000 (Cargill Corp.)
PE-3:Cargill ® 3016 (Cargill Corp.)
PE-4:Cargill ® 3018 (Cargill Corp.)
PE-5:Cargill ® 3020 (Cargill Corp.)
Catalyst:
MTSI-methyl toluene sulfonimide
TK-1 - 1,3-Diacetoxy-1,1,3,3-tetrabutyldistannoxane
DABCO 1,4-Diazabicyclo[2.2.2]octane Two powder coating formulations were electrostatically sprayed on B-1000 panels and cured at 190° C. for 20 minutes. Table 7 illustrates the composition and properties of those coatings along with a coating cured with a prior art crosslinker PowderLink® 1174 (PL-1174) available from CYTEC Industries, West Paterson, N.J.

TABLE 7

| Ingredient (parts by wt.) | 7A | 7B | 7C |
|---|---|---|---|
| Cargill 3000 polyester resin | — | — | 85 |
| Arakote 3109 polyester resin | 94 | — | — |
| Cargill 3018 polyester resin | — | 91 | — |
| Powderlink ® 1174 Crosslinker | 6 | — | — |
| Pyrrolidone Urea Crosslinker (Ex. 16) | — | 9 | 15 |
| R960 Rutile $TiO_2$ DuPont | 40 | 40 | 40 |
| Methyl toluene sulfonamide (MTSI) | 0.5 | No Catalyst | No Catalyst |
| Resiflow ® P67 flow control additive | 1.3 | 1.3 | 1.3 |
| Benzoin | 1.4 | 1.4 | 1.4 |
| Resin/crosslinker | 94/6 | 91/9 | 85/15 |
| Pigment/binder (resin & crosslinker) | 0.4 | 0.4 | 0.4 |
| Gel time, sec. (200° C.) | 358 | 230 | 80 |
| Vertical plate flow, cm (190° C.) | 7.7 | 8.4 | 3.7 |
| Coating Properties/Crosslinker | PL-1174 | Pyrrolidone Urea | Pyrrolidone Urea |
| Substrate (iron phosphate treated CRS) | B1000 | B1000 | B1000 |
| Cure °C./20 minutes | 190° | 190° | 190° |
| Film thickness, mil | 2 | 1.5 | 2 |
| Knoop hardness (25° C.) | 11.9 | 12.0 | 3.0 |
| Impact F/R in.-lb | 160/160 | 160/160 | 50/50 |
| MEK WIPES | 200+ | 200+ | 200+ |
| Gloss 60°/20° | 94/77 | 93/77 | 77/39 |

The data of Table 7 show that films cured by pyrrolidone urea modified melamines are comparable with PL-1174 cured coatings. The cured films have excellent resistance to chemical solvent and possess no pinholes up to 1.5 mil thickness. Coatings cured from Formulation 7C exhibited poor impact properties. Without being bound to any theory, it is believed this result can be attributed to the backbone, Cargill 3000, (which contains more branched polyester than Cargill 3018 and Arakote 3019), since the branched structure tends to given excellent chemical resistance and hardness properties at the sacrifice of impact properties.

EXAMPLE 19

Preparation of Pyrrolidone Urea (N-Carbamylpyrrolidone) From Pyrrolidone and Methyl Carbamate A mixture containing 50 g (0.67 mole) of methyl carbamate, 272 g (3.20 moles) of pyrrolidone, 2.4 g of TK-1 tin catalyst (1,3-diacetoxy-1,1,3,3-Didecylmethylamine-tetrabutyldistannoxane; Aldrich Chemical Company), and 2.4 g of DAMA-10 (didecylmethylamine; Ethyl Corporation) was heated at 140° C. under 40–50 mm Hg pressure for 3.5 hours. The methanol produced by the reaction was collected in a dry ice-acetone trap during the reaction. The reaction mixture was then analyzed with GLC (internal standard method). The results indicated that the yield of pyrrolidone urea was 85% based on methyl carbamate charged, and 10% of the starting methyl carbamate still remained in the reaction mixture. The reaction mixture was then distilled under reduced pressure to remove excess pyrrolidone and the remaining methyl carbamate. The distillation residue was stirred with 200 ml of toluene for 15 minutes and filtered. The collected solid was washed with toluene and weighed 46 g (54%) after it was air-dried; mp 142°–144° C. (lit. mp 142°–143° C.); IR($cm^{-1}$): 3360, 1710, 1660, 1590, 1370, 1250; $^1$H-NMR ($CDCl_3$); δ8.2 (S, 1H), 5.90 (S, 1H), 3.9 (t, 2H), 2.6 (t, 2H), 2.1 (t, 2H).

EXAMPLE 20

Preparation of Pyrrolidone Urea From Pyrrolidone, Urea and Butanol

A mixture containing 30.5 g (0.5 mole) urea, 272 g (3.2 moles) pyrrolidone, 100 ml n-butanol, 2 g TK-1 catalyst, and 2.5 g DAMA-10 is heated at 115° C. for 3 hours with continuous removal of ammonia. The temperature of the reaction mixture is raised to 140° C., butanol and unreacted pyrrolidone are removed under reduced pressure. The residue is stirred with 150 ml of toluene for 15 minutes and filtered. The solid pyrrolidone urea is recovered and washed with toluene and air dried.

Other variations and modifications of this invention will be obvious to those skilled in this art. This invention is not limited except as set forth in the following claims.

We claim:

1. An amino crosslinking agent selected from the group consisting of (i) a triazine compound represented by the formula (I)

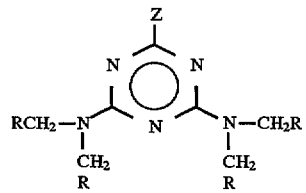

(ii) a glycoluril compound represented by the formula (II)

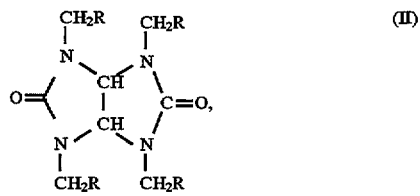

(iii) an oligomer of (i) or of (ii), and
(iv) a mixture of at least two of any of (i), (ii) and (iii),
wherein Z is selected from the group consisting of —N(CH$_2$R)$_2$, aryl having 6 to 10 carbon atoms, alkyl having 1 to 20 carbon atoms, cycloalkyl having 6 to 10 carbons and an acetyl group, and
each R is independently selected from the group consisting of
(a) a substituted urea group represented by the formula

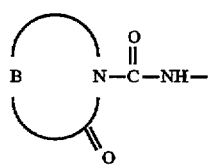

wherein B is an unsaturated or saturated aliphatic ring forming group having 3 to 5 carbon atoms optionally substituted by a keto oxygen, or a bridged aromatic,
(b) an oxime blocked carbamate group represented by the formula

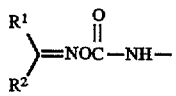

wherein R$^1$ and R$^2$ are independently selected from an alkyl group having 1 to 8 carbon atoms and can together form a cyclic ring having a total of up to 16 carbon atoms including substitution,
(c) —OR$^3$, wherein R$^3$ is hydrogen or an alkyl group having 1 to 12 carbon atoms,
(d)

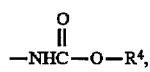

wherein R$^4$ is an alkyl group having 1 to 18 carbon atoms, cycloalkyl group having 6 to 10 carbons or an aryl group having 6 to 20 carbon atoms, and (e)

wherein R$^5$ is hydrogen, an alkyl group having 1 to 18 carbon atoms, cycloalkyl group having 6 to 10 carbons or an aryl group having 6 to 20 carbon atoms, provided that at least one R group is selected from or (b).

2. The amino crosslinking agent according to claim 1, wherein at least two of the R groups are selected from (a) and/or (b).

3. The amino crosslinking agent according to claim 2, wherein at least two of the R groups are selected from the group represented by the formulae

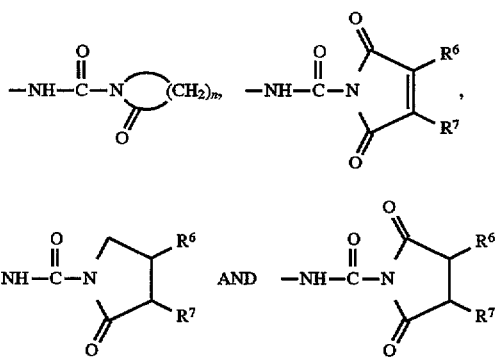

wherein n is 3 to 5, and R$^6$ and R$^7$ are independently hydrogen or alkyl having one to six carbon atoms.

4. The amino crosslinking agent according to claim 3, wherein n is 3 or 5, R$^6$ is hydrogen or methyl and R$^7$ is hydrogen.

5. The amino crosslinking agent according to claim 1, wherein at least two of the R groups are selected from the group consisting of a pyrrolidone urea group, a caprolactam urea group and a maleimido urea group.

6. The amino crosslinking agent according to claim 2, wherein at least two of the R groups are selected from the oxime blocked carbamate group (b) and R$^1$ and R$^2$ are independently selected from an alkyl group having 1 to 6 carbon atoms.

7. The amino crosslinking agent according to claim 6, wherein R$^1$ and R$^2$ are independently methyl or ethyl.

* * * * *

UNITED STATES PATENT AND TRADEMARK OFFICE
CERTIFICATE OF CORRECTION

PATENT NO. : 5,665,852
DATED : September 9, 1997
INVENTOR(S) : Balwant Singh, Laurence W. Chang, Larry S. Anderson, Stephen F. Donovan It is certified that error appears in the above-indentified patent and that said Letters Patent is hereby corrected as shown below:

Column 19, line 39, change "$R^3$" to --$R^2$--.

Column 20, line 10, change "from or" to --from (a) or--.

Signed and Sealed this

Twenty-fifth Day of November, 1997

Attest:

BRUCE LEHMAN

Attesting Officer

Commissioner of Patents and Trademarks